US012580079B2

(12) United States Patent
Singhal et al.

(10) Patent No.: US 12,580,079 B2
(45) Date of Patent: Mar. 17, 2026

(54) PATIENT INVARIANT MODEL FOR FREEZING OF GAIT DETECTION BASED ON EMPIRICAL WAVELET DECOMPOSITION

(71) Applicant: Tata Consultancy Services Limited, Mumbai (IN)

(72) Inventors: Shivam Singhal, Gurgaon (IN); Nasimuddin Ahmed, Kolkata (IN); Varsha Sharma, Kolkata (IN); Sakyajit Bhattacharya, Kolkata (IN); Aniruddha Sinha, Kolkata (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 1051 days.

(21) Appl. No.: 17/684,992

(22) Filed: Mar. 2, 2022

(65) Prior Publication Data

US 2022/0359078 A1    Nov. 10, 2022

(30) Foreign Application Priority Data

Mar. 27, 2021    (IN) .............................. 202121013673

(51) Int. Cl.
*G16H 50/20* (2018.01)
*A61B 5/00* (2006.01)
*A61B 5/11* (2006.01)

(52) U.S. Cl.
CPC ............. *G16H 50/20* (2018.01); *A61B 5/112* (2013.01); *A61B 5/6829* (2013.01);
(Continued)

(58) Field of Classification Search
CPC ........ G16H 50/20; G16H 20/30; G16H 50/70; A61B 5/112; A61B 5/6829; A61B 5/7257;
(Continued)

(56) References Cited

U.S. PATENT DOCUMENTS

| | | | |
|---|---|---|---|
| 10,231,648 B2 | 3/2019 | Plotnik-Peleg et al. | |
| 2014/0276130 A1* | 9/2014 | Mirelman ............ | A61B 5/1104 |
| | | | 600/595 |
| 2018/0206774 A1* | 7/2018 | Huang ................. | A61B 5/7278 |

FOREIGN PATENT DOCUMENTS

| | | | | |
|---|---|---|---|---|
| CN | 112057080 | * | 12/2020 | ........... G06F 18/214 |

OTHER PUBLICATIONS

Omkar Singh et al., "ECG signal denoising via empirical wavelet transform", Australas Phys. Eng. Sci. Med. (2017) 40:219-229.*

(Continued)

*Primary Examiner* — Alexander Satanovsky
(74) *Attorney, Agent, or Firm* — Finnegan, Henderson, Farabow, Garrett & Dunner, LLP

(57) ABSTRACT

This disclosure relates generally to patient invariant model for freezing of gait detection based on empirical wavelet decomposition. The method receives a motion data from an accelerometer sensor coupled to an ankle of a subject. The motion data is further processed to denoise a plurality of data windows using a peak detection technique to classify into a real motion data window or a noisy data window. Further, a plurality of denoised data windows are generated by processing spectrums associated with each real motion data window and a plurality of empirical modes using an empirical wavelet decomposition technique (EWT). Then, a resultant acceleration is computed, and a plurality of features are extracted from the denoised data window which enables (Continued)

detection of freezing of gait based on a pretrained classifier model into a (i) a positive class, or (ii) a negative class.

16 Claims, 7 Drawing Sheets

(52) U.S. Cl.
CPC ............ *A61B 5/7257* (2013.01); *A61B 5/726* (2013.01); *A61B 5/7264* (2013.01); *A61B 5/7282* (2013.01)

(58) Field of Classification Search
CPC ..... A61B 5/726; A61B 5/7264; A61B 5/7282; A61B 5/4082; A61B 5/7203; A61B 5/725; A61B 5/7267; A61B 2562/0219
See application file for complete search history.

(56) References Cited

OTHER PUBLICATIONS

Bhattacharyya et al., "A multivariate approach for patient specific EEG seizure detection using empirical wavelet transform," (2017).
Singh et al., "ECG signal denoising via empirical wavelet transform," Australas Phys Eng Sci Med, 40:219-229 (2017).

* cited by examiner

200

```
┌──────────────────────────────────────────────────────────────┐
│ receiving, a motion data obtained from a sensor coupled to an │
│ ankle of a subject, wherein the sensor captures one or more   │
│ activities performed by the subject, wherein the sensor       │
│ comprises an accelerometer                                    │  202
└──────────────────────────────────────────────────────────────┘
                             │
                             ▼
┌──────────────────────────────────────────────────────────────┐
│ determining using a windowing, a plurality of data windows    │
│ based on the plurality of motion data                         │  204
└──────────────────────────────────────────────────────────────┘
                             │
                             ▼
┌──────────────────────────────────────────────────────────────┐
│ denoising using a peak detection technique, the plurality of  │
│ data windows by detecting total number of peaks associated    │
│ with each data window is denoised using a peak detection      │
│ technique, wherein each window is classified into one of (i) a │
│ real motion data window, if the number of candidate peaks are │  206
│ greater than a predefined value, or (ii) a noisy data window, │
│ wherein discarding the noisy data window, if the number of    │
│ candidate peaks are lesser than or equal to the predefined    │
│ value, wherein the candidate peak is identified if the peak   │
│ height exceeds a predefined threshold                         │
└──────────────────────────────────────────────────────────────┘
                             │
                             ▼
┌──────────────────────────────────────────────────────────────┐
│ generating, using an empirical wavelet decomposition          │
│ technique, a plurality of denoised data windows based on (i) a │
│ spectrum associated with each real motion data window, and    │  208
│ (ii) a plurality of empirical modes;                          │
└──────────────────────────────────────────────────────────────┘
                             │
                             ▼
```

FIG.2A

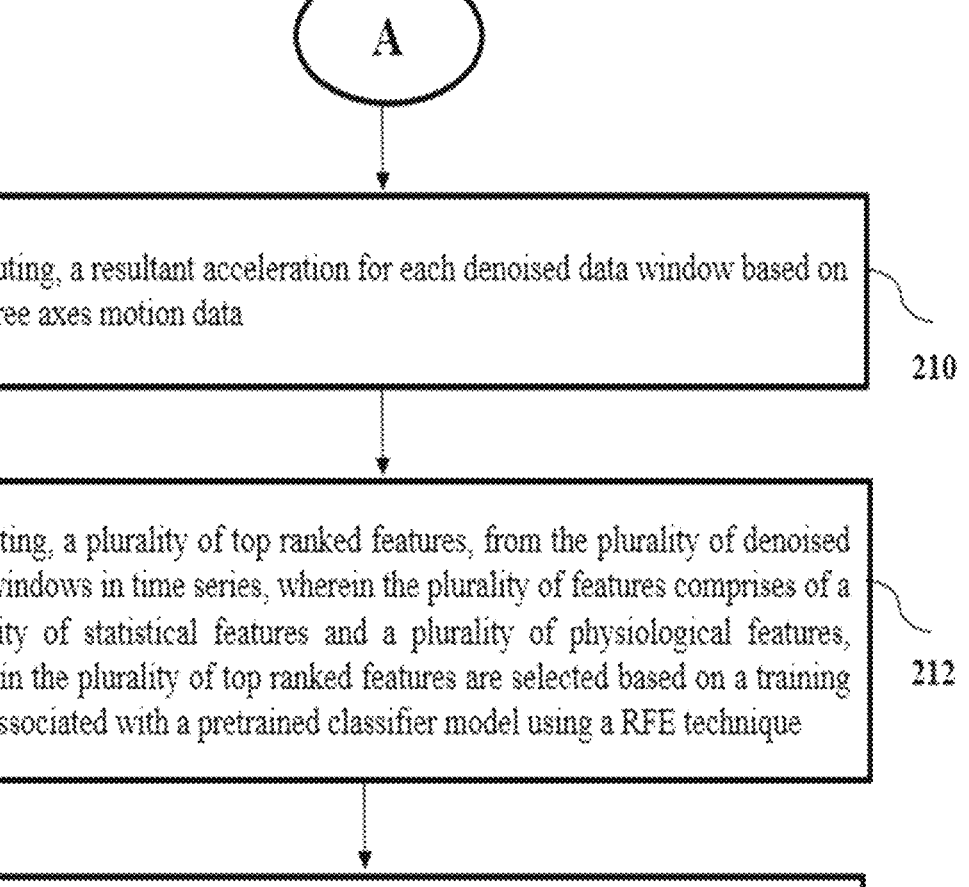

A computing, a resultant acceleration for each denoised data window based on the three axes motion data    210 extracting, a plurality of top ranked features, from the plurality of denoised data windows in time series, wherein the plurality of features comprises of a plurality of statistical features and a plurality of physiological features, wherein the plurality of top ranked features are selected based on a training data associated with a pretrained classifier model using a RFE technique    212 detecting freezing of gait, based on the pretrained classifier model and the plurality of features by classifying each denoised data window into atleast one of (i) a positive class, and (ii) a negative class    214

FIG.2B

PATIENT INVARIANT MODEL FOR FREEZING OF GAIT DETECTION BASED ON EMPIRICAL WAVELET DECOMPOSITION

CROSS-REFERENCE TO RELATED APPLICATIONS AND PRIORITY

This U.S. Patent application claims priority under 35 U.S.C § 119 to: Indian patent Application no. 202121013673, filed on Mar. 27, 2021. The entire contents of the aforementioned application are incorporated herein by reference.

TECHNICAL FIELD

The disclosure herein generally relates to detect gait disorders, and, more particularly, to patient invariant model for freezing of gait detection based on empirical wavelet decomposition.

BACKGROUND

Freezing of gait (FOG) is a paroxysmal gait disturbance, a sudden or transient inability in commencing or continuing ambulation or unpredictable interruption of walking associated with a Parkinson's disease. Episodes of FOG impedes gait and augments fall propensity which often leads to serious fall-injury. Sporadic FOG episodes are often associated with concomitant falls which could result injury and demean the quality of life. Pharmacological treatment yields transient relief where the effect gradually wears off. Hence, information on progressive symptomatic changes in patients aids the neurologists in personalizing therapy. During in clinic assessment, FOG questionnaire (FOG-Q) based evaluation performed by trained personnel is ineffective, as the freezing episodes do not occur in repetitive or deterministic manner. FOG initiation is highly related to environmental factors or cognitive state of the patient, thus evoking in clinics is quite an impractical task. Clinicians usually rely on self-reporting of the patient which is erroneous and futile. Hence, detection and assessment of FOG in the home environment is of vital importance for adequate prognosis and effective management of treatment. Moreover, online detection of FOG could be beneficial for an assistive system that provides rhythmical cueing in the form of auditory, visual or haptic stimulation to prevent FOG.

Wearable sensors such as Inertial Motion Unit (IMU) and insole foot sensors is currently emerged for the gait analysis due to availability in wearable form factor. Insole foot sensors, incorporating multiple force-sensing resistors or piezoelectric transducers, measure the plantar pressure. IMU captures movement variation in the mediolateral, anteroposterior and vertical direction. Combining these two sensors impart a great insight on the dynamics of the gait. However, the condition of FOG patients and their limitation is desired to limit the number of sensors. In view of the convenience of the patient, the ankle borne IMU sensor is sensor modality. During gait, the motion in the lower limb, closest to the ground, is maximum. Thus, among multiple locations, the ankle IMU data sensor provides enriched dynamics between a normal gait and a FOG.

Many conventional techniques for FOG detection using the wearable sensors employs a machine learning or a deep learning based approaches to detect FOG. Considering the individualistic pattern in human gait, most of the existing techniques on FOG principally focus on the patient dependent model. However, constructing the model for every individual is quite an arduous task and many patients do not perceive any FOG episodes in the clinical setup. In such scenario, a patient independent or invariant model is necessary would be beneficial for practical deployment of wearable sensor.

SUMMARY

Embodiments of the present disclosure present technological improvements as solutions to one or more of the above-mentioned technical problems recognized by the inventors in conventional systems. For example, in one embodiment, a system for patient invariant model for freezing of gait detection based on empirical wavelet decomposition is provided. The system includes receiving, a motion data obtained from a sensor coupled to an ankle of a subject, wherein the sensor captures one or more activities performed by the subject, wherein the sensor comprises an accelerometer. Further, a windowing function is utilized to determine a plurality of data windows from the motion data. Each data window is denoised using a peak detection technique, wherein each window is classified into one of (i) a real motion data window, if the number of candidate peaks are greater than a predefined value, or (ii) a noisy data window, wherein discarding the noisy data window, if the number of candidate peaks are lesser than or equal to the predefined value, wherein the candidate peak is identified if the peak height exceeds a predefined threshold. Then, a resultant acceleration for each denoised data window is computed based on the three axes motion data. Further, extracting a plurality of top ranked features, from the plurality of denoised data windows in time series, wherein the plurality of top ranked features comprises of a plurality of statistical features and a plurality of physiological features, wherein the plurality of top ranked features are selected based on a training data associated with a pretrained classifier model using a RFE technique. Furthermore, freezing of gait is detected based on the pretrained classifier model and the plurality of top ranked features by classifying each denoised data window into at least one of (i) a positive class, and (ii) a negative class.

In one embodiment, the empirical wavelet decomposition technique, a plurality of denoised data windows are generated based on spectrums obtained from the motion data and partitioned into a plurality of contiguous segments, wherein the spectrums are obtained by applying Fourier transform. Further, a one or more empirical wavelets for each segment are constructed based on a segment boundary and a scaling function derived for each empirical wavelet based on a low pass filter and a band pass filter. The one or more empirical wavelets are decomposed into at least one of each empirical mode from the plurality of empirical modes. The plurality of denoised data windows are generated based on the empirical modes which have low frequency components, wherein selecting the first three empirical modes from the plurality of empirical modes which includes only low frequency components.

The plurality of physiological features includes a mean frequency, a median frequency, a freezing of gait power, a motion power and a freezing index. The plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value. In another embodiment, the mean frequency is computed based on a frequency value and a spectral power of a power spectrum at each frequency bin. The median frequency is computed based on the frequency value at which the power spectrum is divided into two regions with equal integral of the power.

In another aspect, a method for patient invariant model for freezing of gait detection based on empirical wavelet decomposition is provided. The method includes receiving, a motion data obtained from a sensor coupled to an ankle of a subject, wherein the sensor captures one or more activities performed by the subject, wherein the sensor comprises an accelerometer. Further, a windowing function is utilized to determine a plurality of data windows from the motion data. Each data window is denoised using a peak detection technique, wherein each window is classified into one of (i) a real motion data window, if the number of candidate peaks are greater than a predefined value, or (ii) a noisy data window, wherein discarding the noisy data window, if the number of candidate peaks are lesser than or equal to the predefined value, wherein the candidate peak is identified if the peak height exceeds a predefined threshold. Then, a resultant acceleration for each denoised data window is computed based on the three axes motion data. Further, extracting a plurality of top ranked features, from the plurality of denoised data windows in time series, wherein the plurality of features comprises of a plurality of statistical features and a plurality of physiological features, wherein the plurality of top ranked features are selected based on a training data associated with a pretrained classifier model using the RFE technique. Furthermore, freezing of gait is detected based on the pretrained classifier model and the plurality of top ranked features by classifying each denoised data window into at least one of (i) the positive class, and (ii) the negative class.

In one embodiment, the empirical wavelet decomposition technique, a plurality of denoised data windows are generated based on spectrums obtained from the motion data into a plurality of contiguous segments, wherein the spectrums are obtained by applying Fourier transform. Further, a one or more empirical wavelets for each segment are constructed based on a segment boundary and a scaling function derived for each empirical wavelet based on a low pass filter and a band pass filter. The one or more empirical wavelets are decomposed into at least one of each empirical mode from the plurality of empirical modes. The plurality of denoised data windows are generated based on the empirical modes which have low frequency components, wherein selecting the first three empirical modes from the plurality of empirical modes which includes only low frequency components.

The plurality of physiological features includes a mean frequency, a median frequency, a freezing of gait power, a motion power and a freezing index. The plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value. In another embodiment, the mean frequency is computed based on a frequency value and a spectral power of a power spectrum at each frequency bin. The median frequency is computed based on the frequency value at which the power spectrum is divided into two regions with equal integral of the power.

In yet another aspect, provides one or more non-transitory machine readable information storage mediums comprising one or more instructions, which when executed by one or more hardware processors perform actions includes receiving, a motion data obtained from a sensor coupled to an ankle of a subject, wherein the sensor captures one or more activities performed by the subject, wherein the sensor comprises an accelerometer. Further, a windowing function is utilized to determine a plurality of data windows from the motion data. Each data window is denoised using a peak detection technique, wherein each window is classified into one of (i) a real motion data window, if the number of candidate peaks are greater than a predefined value, or (ii) a noisy data window, wherein discarding the noisy data window, if the number of candidate peaks are lesser than or equal to the predefined value, wherein the candidate peak is identified if the peak height exceeds a predefined threshold. Then, a resultant acceleration for each denoised data window is computed based on the three axes motion data. Further, extracting a plurality of top ranked features, from the plurality of denoised data windows in time series, wherein the plurality of features comprises of a plurality of statistical features and a plurality of physiological features, wherein the plurality of top ranked features are selected based on a training data associated with a pretrained classifier model using the RFE technique. Furthermore, freezing of gait is detected based on the pretrained classifier model and the plurality of top ranked features by classifying each denoised data window into at least one of (i) the positive class, and (ii) the negative class.

In one embodiment, the empirical wavelet decomposition technique, a plurality of denoised data windows are generated based on spectrums obtained from the motion data into a plurality of contiguous segments, wherein the spectrums are obtained by applying Fourier transform. Further, a one or more empirical wavelets for each segment are constructed based on a segment boundary and a scaling function derived for each empirical wavelet based on a low pass filter and a band pass filter. The one or more empirical wavelets are decomposed into at least one of each empirical mode from the plurality of empirical modes. The plurality of denoised data windows are generated based on the empirical modes which have low frequency components, wherein selecting the first three empirical modes from the plurality of empirical modes which includes only low frequency components.

The plurality of physiological features includes a mean frequency, a median frequency, a freezing of gait power, a motion power and a freezing index. The plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value. In another embodiment, the mean frequency is computed based on a frequency value and a spectral power of a power spectrum at each frequency bin. The median frequency is computed based on the frequency value at which the power spectrum is divided into two regions with equal integral of the power.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 2A and FIG. 2B is a flow diagram of a method to detect FOG disorder of a subject by denoising motion data using an Empirical wavelet decomposition technique (EWT) using the system of FIG. 1, in accordance with some embodiments of the present disclosure.

DETAILED DESCRIPTION OF EMBODIMENTS

Figure 1:
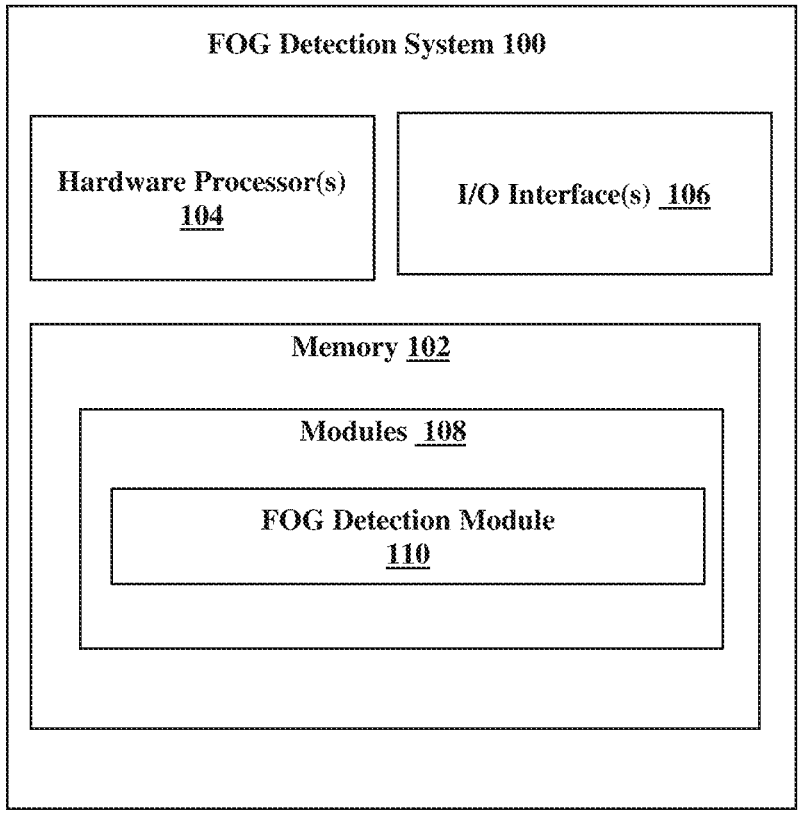
FIG. 1 illustrates an exemplary freezing of gait (FOG) detection system, in accordance with some embodiments of the present disclosure.
Figure 3:
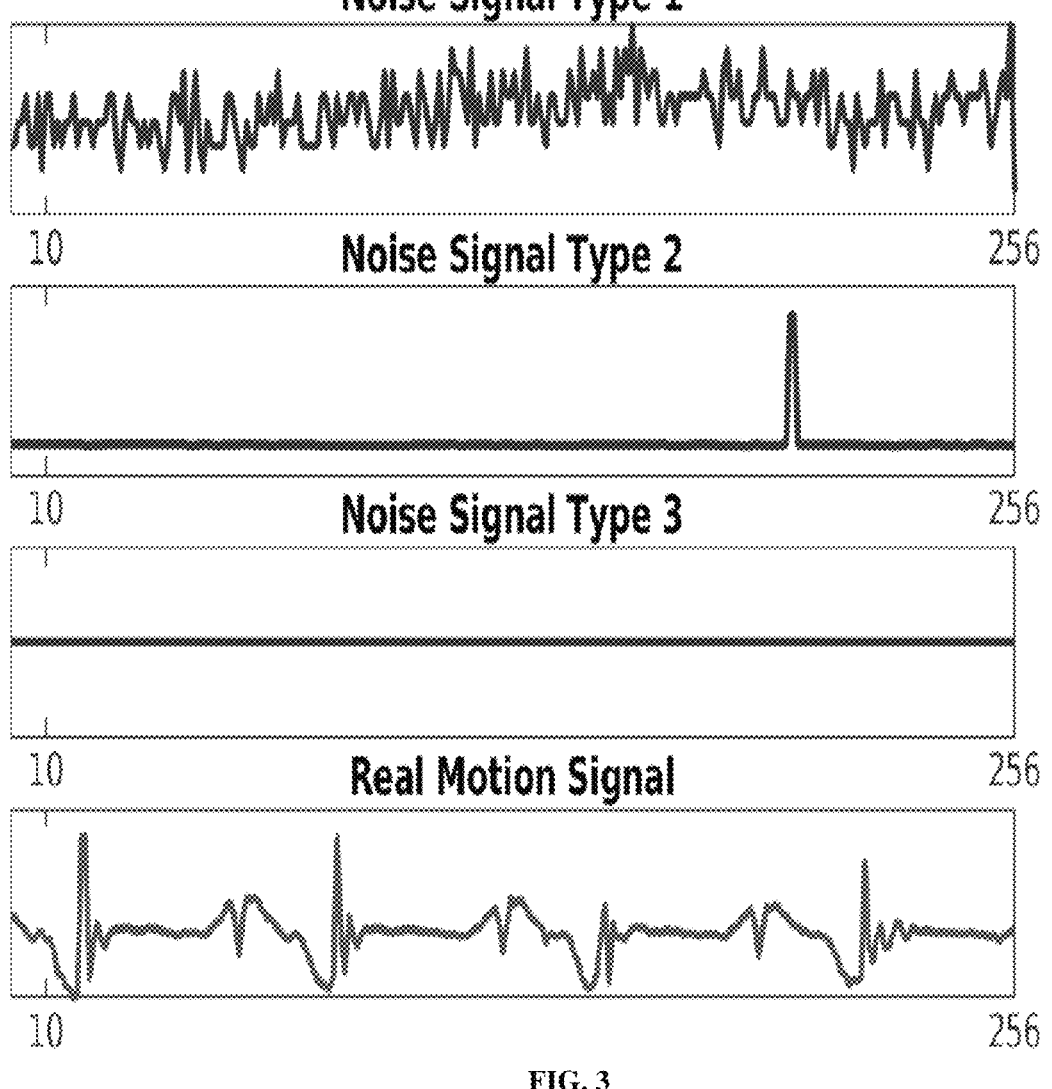
FIG. 3 is a set of example graphs schematically showing a noisy data window and a real motion data window of the motion data using the system of FIG. 1, in accordance with some embodiments of the present disclosure.
Figure 4:
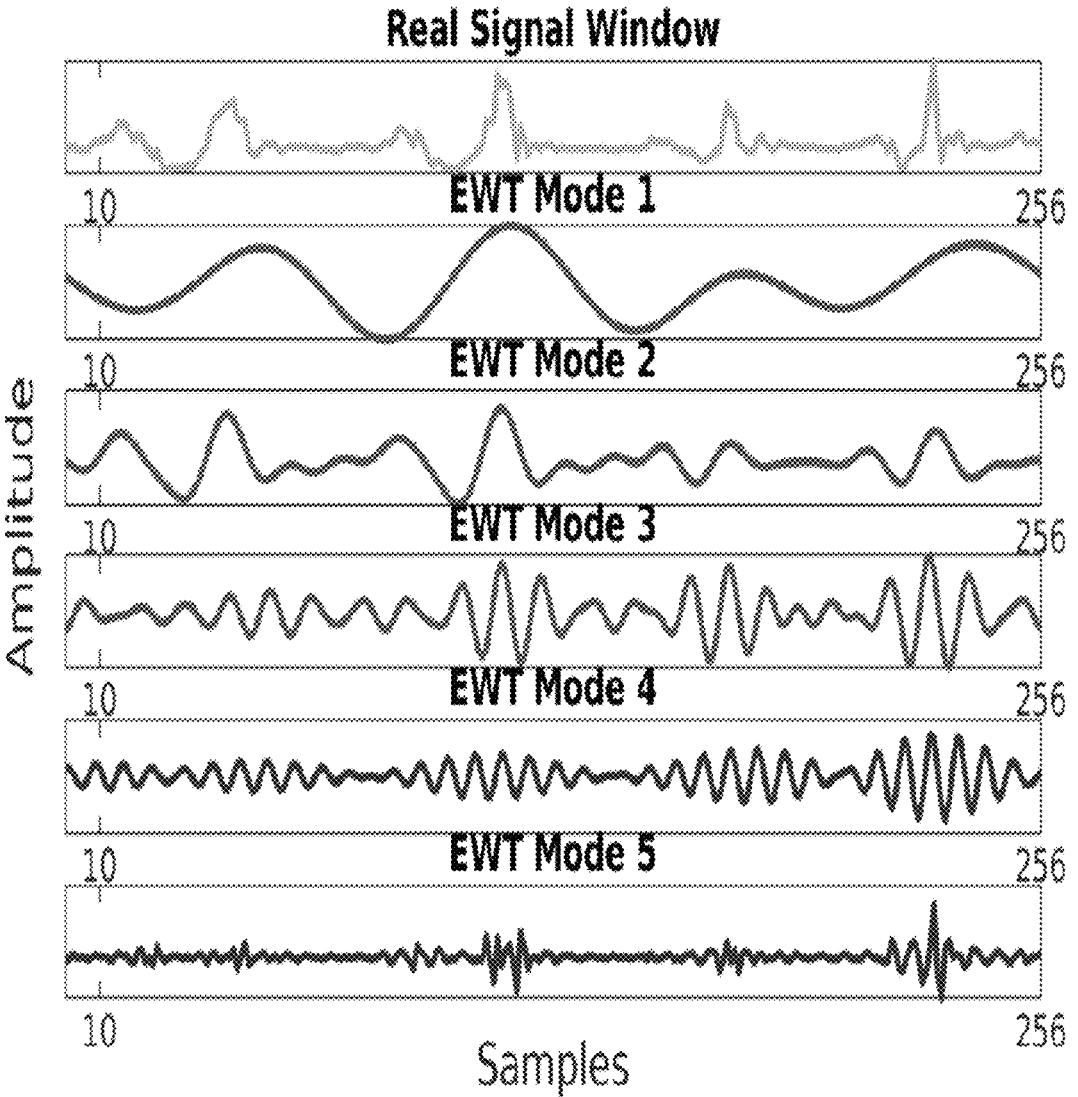
FIG. 4 illustrates graphical representation of the motion data window with its corresponding empirical modes, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provides a method and a system to detect freezing of gait (FOG) disorder of a subject by denoising motion data using an Empirical wavelet decomposition technique (EWT). The system enables online detection of freezing of gait (FOG) using a wearable motion sensor. The system may be alternatively referred as a FOG detection system. The method disclosed is a patient independent model leveraged with a single ankle sensor which makes more feasible approach in terms of usability. Further, the method disclosed utilizes a wearable accelerometer sensor connected to the ankle of a subject to receive a motion data. The accelerometer sensor captures the motion data in real time for detection of FOG which includes one or more activities performed by the subject. The received motion data is further processed to determine a plurality of data windows. Further, the plurality of data windows are denoised using a peak detection technique, wherein each window is classified into one of (i) a real motion data window, if the number of candidate peaks are greater than a predefined value, or (ii) a noisy data window, wherein discarding the noisy data window, if the number of candidate peaks are lesser than or equal to the predefined value, wherein the candidate peak is identified if the peak height exceeds a predefined threshold. The system is employed with an Empirical wavelet decomposition technique (EWT) processes the plurality of data windows to obtain a plurality of denoised data windows. Further, a resultant acceleration is computed based on a 3 axis motion data to detect freezing of gait based on a pretrained classifier model and a plurality of top ranked features by classifying each denoised data window into at least one of (i) a positive class, or (ii) a negative class. However, the disclosed system provides people agnostic approach as described in conjunction with FIG. 1 to FIG. 5B below.

Referring now to the drawings, and more particularly to FIG. 1 through FIG. 5B, where similar reference characters denote corresponding features consistently throughout the figures, there are shown preferred embodiments and these embodiments are described in the context of the following exemplary system and/or method.

FIG. 1 illustrates an exemplary freezing of gait (FOG) detection system, in accordance with some embodiments of the present disclosure. In an embodiment, the FOG detection system 100 includes processor (s) 104, communication interface (s), alternatively referred as or input/output (I/O) interface(s) 106, and one or more data storage devices or memory 102 operatively coupled to the processor (s) 104. The system 100, with the processor(s) is configured to execute functions of one or more functional blocks of the system 100. Referring to the components of the system 100, in an embodiment, the processor (s) 104 can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the processor(s) 104 is configured to fetch and execute computer-readable instructions stored in the memory. In an embodiment, the system 100 can be implemented in a variety of computing systems, such as laptop computers, notebooks, 10 hand-held devices, workstations, mainframe computers, servers, a network cloud, and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server. The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The memory 102 comprises a plurality of modules 108 that includes a FOG detection module 110. The modules 108 can be an Integrated Circuit (IC) (not shown), external to the memory 102, implemented using a Field-Programmable Gate Array (FPGA) or an Application-Specific Integrated Circuit (ASIC). The names (or expressions or terms) of the modules of functional block within the modules 108 referred herein, are used for explanation and are not construed to be limitation(s). The modules 108 includes the FOG detection module 110 for processing the motion data as inputs received from accelerometer sensor connected to the ankle of the subject. The present disclosure is further explained considering an example, where the system 100 detects the FOG from the motion data of the subject using the system of FIG. 1. Further, the memory 102 may comprises information pertaining to input(s)/output(s) of each step performed by the processor(s) 104 of the system 100 and methods of the present disclosure. Functions of the components of system 100, for detection of FOG from the motion data, are explained in conjunction with FIG. 2A through FIG. 5B providing flow diagram, architectural overviews, and performance analysis of the system 100.

FIG. 2A and FIG. 2B is a flow diagram of a method to detect FOG disorder of a subject by denoising motion data using an Empirical wavelet decomposition technique (EWT) using the system of FIG. 1, in accordance with some embodiments of the present disclosure. In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIG. 1 and the steps of flow diagram as depicted in FIG. 2A and FIG. 2B. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring now to the steps of the method 200, at step 202, the one or more hardware processors 104, receiving a motion data obtained from a sensor coupled to an ankle of a subject, wherein the sensor captures one or more activities performed by the subject, wherein the sensor comprises an accelerometer. The one or more activities may be walking, sitting, standing and any such actions performed by the subject. The method detects the occurrence of FOG from the motion data by identifying varying patterns or the one or more activities performed by the subject. Considering an example, where the system is obtaining the motion data from a wearable sensor comprising an accelerometer connected to the ankle of the subject. The accelerometer sensor sends the one or more activities performed by the subject in real time. The system further processes the motion data to detect the FOG.

Referring now to the steps of the method 200, at step 204, the one or more hardware processors 104, determining using a windowing, a plurality of data windows based on the motion data. Here, the received motion data is processed by performing the windowing function to determine the plurality of data windows. Each data window includes the motion data to get a full data window. As an initial step, 4-second sliding window with the overlap of 75% is required for data windowing and each data window is represented in Equation 1, $$\{[A1_x, A1_y, A1_z], [A2_x, A2_y, A2_z] \ldots, [An_x, An_y, An_z]\}$$
<div align="right">Equation (1)</div>

$Ai_x$—acceleration X value for $i^{th}$ sample of the data window $Ai_y$—acceleration Y value for $i^{th}$ sample of the data window $Ai_z$—acceleration Z value for $i^{th}$ sample of the data window wherein, the dimension is represented in [n rows*3 columns].

Referring now to the steps of the method 200, at step 206, the one or more hardware processors 104, denoising using a peak detection technique, the plurality of data windows by detecting total number of peaks associated with each data window is denoised using a peak detection technique, wherein each window is classified into one of (i) a real motion data window, if the number of candidate peaks are greater than a predefined value, or (ii) a noisy data window, wherein discarding the noisy data window, if the number of candidate peaks are lesser than or equal to the predefined value, wherein the candidate peak is identified if the peak height exceeds a predefined threshold. Referring now to (FIG. 3), from the received motion data each data window is classified into the real motion data window or the noisy data window and then the noisy data windows are discarded. The predefined value is represented as one. The predefined threshold is estimated empirically based on the real motion data window and the noisy data window. Initially, from each window the total number of peaks are detected using the peak detection technique. Further, one or more candidate peaks are identified if the peak height exceeds the predefined threshold, which has been estimated empirically. The noisy data windows are identified if the number of candidate peaks are lesser than or equal to one, then such data window is classified as the noisy data window, and thus discarded.

Referring now to the steps of the method 200, at step 208, the one or more hardware processors 104, generating using an empirical wavelet decomposition technique (EWT), a plurality of denoised data windows based on (i) a spectrum associated with each data window, and (ii) a plurality of empirical modes. Here, each data window is denoised using the EWT approach employed in the system 100. Referring now to the above considered example, the plurality of data windows are processed to generate the plurality of denoised windows. Inherently, human movement related signals captured by the accelerometer sensor is non-stationary in nature and cluttered with high-frequency noises. To denoise such motion data, the EWT performs the following steps, from each data window, spectrums are obtained from the motion data by applying Fourier transform which are further segmented into a plurality of contiguous segments. Referring now to the example, the accelerometer sensor inputs includes the motion data represented as samples X={x_1, x_2, x_3, ... x_N}, wherein 'N' is the total number of data samples. The spectrum of each motion data is defined as Equation 2, $$X(f)\mathcal{F}\ (X(n))$$
<div align="right">Equation (2)</div> where $\mathcal{F}$ ' denotes the Fourier transform and f $\in$ [0,N]. Next, the spectrum obtained from each data window of the motion data segmented into the plurality of contiguous segments (K). These contiguous segments are represented below in Equation 3, $$P_i=[w_{i-1}, w_i]$$
<div align="right">Equation (3)</div>

Where, 'i'=0,1,2, ... K−1 and $w_o$=0, $w_K$=$\pi$, 'w_1' represents the upper boundary of the segment 'i'.

Further, one or more empirical wavelets for each segment is constructed based on a segment boundary and a scaling function derived for each empirical wavelet based on a low pass filter and a band pass filter. Based on the boundaries of the segments, the empirical wavelets are defined as the bank of wavelet filters, comprised of one low pass filter (scaling function $\phi_1(f)$ and the K−1; bandpass filters ($\psi_{i(f)}$).

Further, the one or more empirical wavelets are decomposed into a plurality of empirical modes, following the classical wavelet theory, the approximation represented in Equation 4, $$(W_o(f)=X(f)^*\phi_i(f))$$
<div align="right">Equation (4)</div> and detail coefficients represented in Equation 5, are computed.

$$(W_i(f)=X(f)*\psi_i(f)) \tag{Equation (5)}$$

Further, the one or more empirical wavelets are decomposed into the plurality of empirical modes represented below in Equation 6 and Equation 7, $$x_o(n)\mathcal{F}^{-1}(W_o(f)*\phi_{i(f)}) \tag{Equation (6)}$$

$$x_i(n)\mathcal{F}^{-1}(W_i(f)*\psi_{i(f)}) \tag{Equation (7)}$$

where, $i\epsilon[1, K-1].\mathcal{F}^{-1}$ denotes the Inverse Fourier transform.

Further, the original motion data X(n) could be obtained as represented in Equation 8, $$X(n)=\Sigma_{i=0}{}^k x_i(n) \tag{Equation (8)}$$

Analytically, certain modes encompass the pertinent features of the real motion data window which needs to be segregated from irrelevant modes. In general, the average human movement is a low frequency span in the range of about (0.6 Hz to 2 Hz). The frequency range for freezing, extends to about 8 Hz and with this criteria the modes associated with high frequency components in the data window. EWT is only associated with the approximations, the low-frequency components of the empirical wavelets.

Further, the plurality of denoised data windows are generated based on the empirical mode which have low frequency components, wherein the first three empirical modes are selected which comprises only low frequency components. The plurality of empirical modes are precisely related to the approximations of the data window at different decomposition level. The experimental analysis results that the first three modes of EWT are mostly pertaining to the relevant low-frequency information of the denoised data window. It has been postulated that these three empirical modes would be adequate to generate the plurality of denoised data windows or a clean signal for each motion data. Notably, the number of modes is empirically identified and apposite to this dataset only.

Referring now to the steps of the method 200, at step 210, the zone or more hardware processors 104, computing resultant acceleration for each denoised data window based on the three axes motion data. From each data window of the motion data as referred above i.e., the resultant acceleration $A_r$ is computed in Equation 9, $$A_r=\sqrt{(A_x)*(A_x)+(A_y)*(A_y)+(A_z)*(A_z)} \tag{Equation (9)}$$

The format of the single data window is represented as Equation 10, $$\{[A1_x, A1_y, A1_z, A1_r], [A2_x, A2_y, A2_z, A2_r], \ldots [An_x, An_y, An_z, An_r]\} \tag{Equation (10)}$$

$Ai_r$—acceleration resultant value of the $i^{th}$ sample of data window

Referring now to the steps of the method 200, at step 212, the one or more hardware processors 104, extracting a plurality of top ranked features, from the plurality of denoised data windows in time series, wherein the plurality of top ranked features comprises of a plurality of statistical features and a plurality of physiological features, wherein the plurality of top ranked features are selected using a RFE technique. The plurality of denoised data windows pertinent information and the plurality of top ranked features are extracted from the time series windows. The 3D motion data along with the resultant data are leveraged to create the input matrix for each window.

The input matrix is represented in Equation 11 as, $$[ACC_x, ACC_y, ACC_z, \text{Resultant}]\epsilon R^{n*K} \tag{Equation (11)}$$

Where 'n' is the no of accelerometer data (samples) or the motion data in the data window and 'K' is the number of inputs. Here, from the plurality of features only top ranked 15 features are computed which have been selected using the RFE technique.

The format of the data window is represented in Equation 12, $$[fs1_j, fs2_j, \ldots fs15_j] \tag{Equation (12)}$$

Where, $fsm_j$ is the $m^{th}$ selected feature for $j^{th}$ data window. Where, the Dimension: 1 row*15 columns. The motion data format is represented in Equation 13, $$\{[fs1_1, fs2_1, \ldots fs15_1], [fs1_2, fs2_2, \ldots fs15_2] \ldots [fs1_k, fs2_k, \ldots fs15_k]\} \tag{Equation (13)}$$

Where, $fs1_j$ is the first selected features of $j^{th}$ data window. The plurality of top ranked features comprises of the plurality of statistical features and the plurality of physiological features. The plurality of statistical features includes a mean, a median, a standard deviation, a maximum value, a minimum value, and a range. Here, the maximum value is the highest value computed from the motion data and the resultant acceleration data. The minimum value is the lowest value computed from the motion data and the resultant acceleration data. The range is the difference between the maximum value and the minimum value. Further, the plurality of physiological features includes a mean frequency, a median frequency, a freezing of gait power, a motion power and a freezing index. Here, the mean frequency ($f_{mean}$) is computed based on a frequency value and a spectral power of a power spectrum at each frequency bin as denoted below in Equation 14, $$f_{mean} = \frac{\sum_{k=0}^{N} P_k * f_k}{\sum_{k=0}^{N} P_k} \tag{Equation (14)}$$

Where, '$P_k$' is the spectral power of power spectrum, '$f_k$' is the frequency value, and 'N' is the total number of bins. The median frequency is computed based on the frequency value at which the power spectrum is divided into two regions with equal integral of the power. Further, the mean frequency and the median frequency improves the accuracy of the generic model. Further, the plurality of top ranked features is selected that essentially improves the performance of the classifier model using the Recursive feature elimination (RFE) technique implemented and reduces computational complexity. Here, the total number of the plurality of top ranked features were calculated, after which the RFE was performed in the offline mode. Firstly, the feature data of all subjects are combined, which is then splitted into 80% of the training data and 20% of the testing data. The training data set is then used to rank all the 44 features using the RFE. Top 15 features (the Freezing Index, the FOG Power, the mean and the median Frequency, the statistical mean, and the standard deviation) which provides the best performance and further used for classification using the classifier model.

Referring now to the steps of the method 200, at step 214, the one or more hardware processors 104, detecting freezing of gait, based on the pretrained classifier model and the plurality of top ranked features by classifying each denoised data window into at least one of (i) a positive class, and (ii) a negative class. In one embodiment, building the classifier model includes generating the training dataset using a public dataset (Daphnet) to develop and validate the EWT. The Daphnet dataset comprises of 500 minutes of the accelerometer sensor data or the motion data (sampled at 64 Hz) which was recorded using 3 accelerometer sensors attached to the shank (just above the ankle), thigh and the lower back of each subject. Further, 10 PD subjects (7 males and 3 females; Age: $66:5\pm4:8$ Y), with symptoms of FOG for analysis. For experimental analysis, the data recorded using the accelerometer sensor, attached to the shank of the subject were utilized. As the subject number 4 and the subject number 10 did not have any FOG episode and the same has been excluded. The Daphnet dataset consists of total 237 FOG events ($23.7\pm20.7$, per subject), with duration ranging from 0.5 to 40.5 seconds ($7.3\pm6.7$ seconds, per subject). Further, in the training data each accelerometer sample comprises of a ground truth label wherein, the format of the single accelerometer data sample is represented as Equation 15, $$[A_x A_y A_z GT] \qquad \text{Equation (15)}$$

Further, for the motion data, the windowing function is performed to determine the plurality of training data windows. The format of the training data window after windowing is represented in Equation 16, $$\{[A1_x, A1_y, A1_z, GT_1], [A2_x, A2_y, A2_z, GT_2] \ldots$$
$$[An_x, An_y, An_z, GT_i]\} \qquad \text{Equation (16)}$$

Where, $GT_i$, is the ground truth label of the $i^{th}$ sample of the data window.

Further, building the classifier model includes the window annotation, where each data window will have the ground truth label equal to zero or one. Here, a single ground truth label is assigned to each data window based on, if for a data window at least 60% of $\{GT_1, GT_2, GT_3 \ldots GT_n\}$ is equal to one, then a label equal to one is assigned to this data window, otherwise zero is assigned to the label to this window. i.e., if 60% of the accelerometer samples in the data window belongs to FOG class so this data window belongs to FOG class. Here, each data window after annotation is represented in Equation 17 as, $$\{[[A1_x, A1_y, A1_z, A1_r], [A1_x, A2_y, A2_z, A2_r], \ldots,$$
$$[An_x, An_y, An_z, An_r]]GT_j\} \qquad \text{Equation (17)}$$

$GT_j$: ground truth label for $j^{th}$ data window.

Further for each data window, denoising is performed using the peak detection technique. If the peak height exceeds the certain minimum threshold then it is chosen as the candidate peak. For the noisy data window, the number of candidate peaks never exceeds more than one. The threshold has been estimated empirically by analyzing the noisy data window and the real motion data window. Then, the EWT as specified above will be performed during the training phase for denoising each data window. Referring now to (FIG. 4), which depicts the data window of the ankle IMU signal in various empirical modes. Also, it is experimented that the first three modes have low frequency components for further processing and the high frequency modes are discarded. Essentially, the reconstructed denoised data window is represented in Equation 18, $$X_c(n) = \Sigma_{i=0}^2 x_i(n) \qquad \text{Equation (18)}$$

which can be utilized for extracting the plurality of training data features.

Further, for each training data window the resultant acceleration is computed based on the three axes motion data. From each data window of the motion data as referred above i.e., the resultant acceleration $A_r$ is computed. Further, the plurality of training data features is computed for each training data window, wherein for all the plurality of features each of the column of the data window (i.e., X, Y, Z and resultant acceleration). So, 11*4=44 features for one data window are obtained where each data window can be represented in a single row. The format for $j^{th}$ data windows as in Equation 19, $$[f1_j, f2_j, \ldots, f44_j, GT_j] \qquad \text{Equation (19)}$$

Dimension: 1 row*45 columns, in training phase all the plurality of training data features are computed. Further, the plurality of training data features is ranked and selected based on the training data associated with the classifier model using the RFE technique as referred in Equation 20, $$[fs1_j, fs2_j, \ldots, fs15_j, GT_j] \qquad \text{Equation (20)}$$

Assuming, all the data windows with ground truth label, where

No. of data windows with GT label equal to 1=$W_p$

No. of data windows with GT label equal to 0=$W_n$

If there is large difference between $W_p$ and $W_n$, then this is called as class imbalance (no of data windows belonging to one class is much larger than the number of windows belonging to the other class). Considering the infrequent occurrence of FOG, the training data is highly imbalanced. So using the 'Random Under-sampling', randomly select and eliminate the windows (of class which has more windows) belonging to class 0/class 1 (according to whichever of $W_n$ or $W_p$ is higher) until the dataset is balanced. After this step, the number of windows belonging to each class would be equal. Instead of random under sampling, other sophisticated sampling methods could be used. Moreover, random under sampling reduces the computational overhead and has provided satisfactory results. Based on all the features, the classifier model is built to classify the motion data into either one of the positive class or the negative class.

In one embodiment, in accordance with the generic model (patient independent), the experiment using leave-one-subject-out techniques (LOSO) was done. It utilizes N−1 subjects' data for training and the remaining one subject's data for testing. This is repeated for all the subjects. The FOG detection is classified into two class classification problem, where FOG (F) is denoted as the positive class and Motion (M) is described as negative class. The random forest classifier with 10-fold cross validation is employed to obtain the classification result.

To evaluate, the performance of the patient independent model, two kinds of experimental analysis were conducted: 1) Comparative analysis with the current state of the arts, and 2) Feature analysis. The performance of FOG detection is evaluated using the two performance metric Sensitivity, $$\left(SN = \frac{TP}{TP + FN}\right)$$

and Specificity $$\left(SP = \frac{TN}{TN + FP}\right)$$

which are extensively used in the existing techniques for evaluation. Extending the formal definition of classes SN measures the proportion of FOG windows that are correctly detected, whereas SP relates to the proportion of Motion windows that are identified correctly.

In one embodiment, the comparative analysis of the proposed method with the existing techniques represents benchmark for the EWT tabulating the comparative result in Table 1.

TABLE 1

| Comparative results with existing techniques | | | | |
| --- | --- | --- | --- | --- |
| | SN ± std | SP ± std | WS | CW |
| Existing technique 1 (Bachlin) | 0.73 | 0.82 | 4 | |
| Existing technique 2 (Mazilu) | 0.66 | 0.95 | 4 | |
| Existing technique 3 (San-R1) | 0.95 | 0.74 | 4 | 3PW & 3SW |
| Existing technique 4 (San-R2) | 0.95 | 0.72 | 4 | 3PW |
| Proposed (Algo-R1) | 0.95 ± 0.05 | 0.70 ± 0.12 | 4 | |
| Proposed (Algo-R2) | 0.83 ± 0.09 | 0.83 ± 0.07 | 4 | |

Figure 5A:
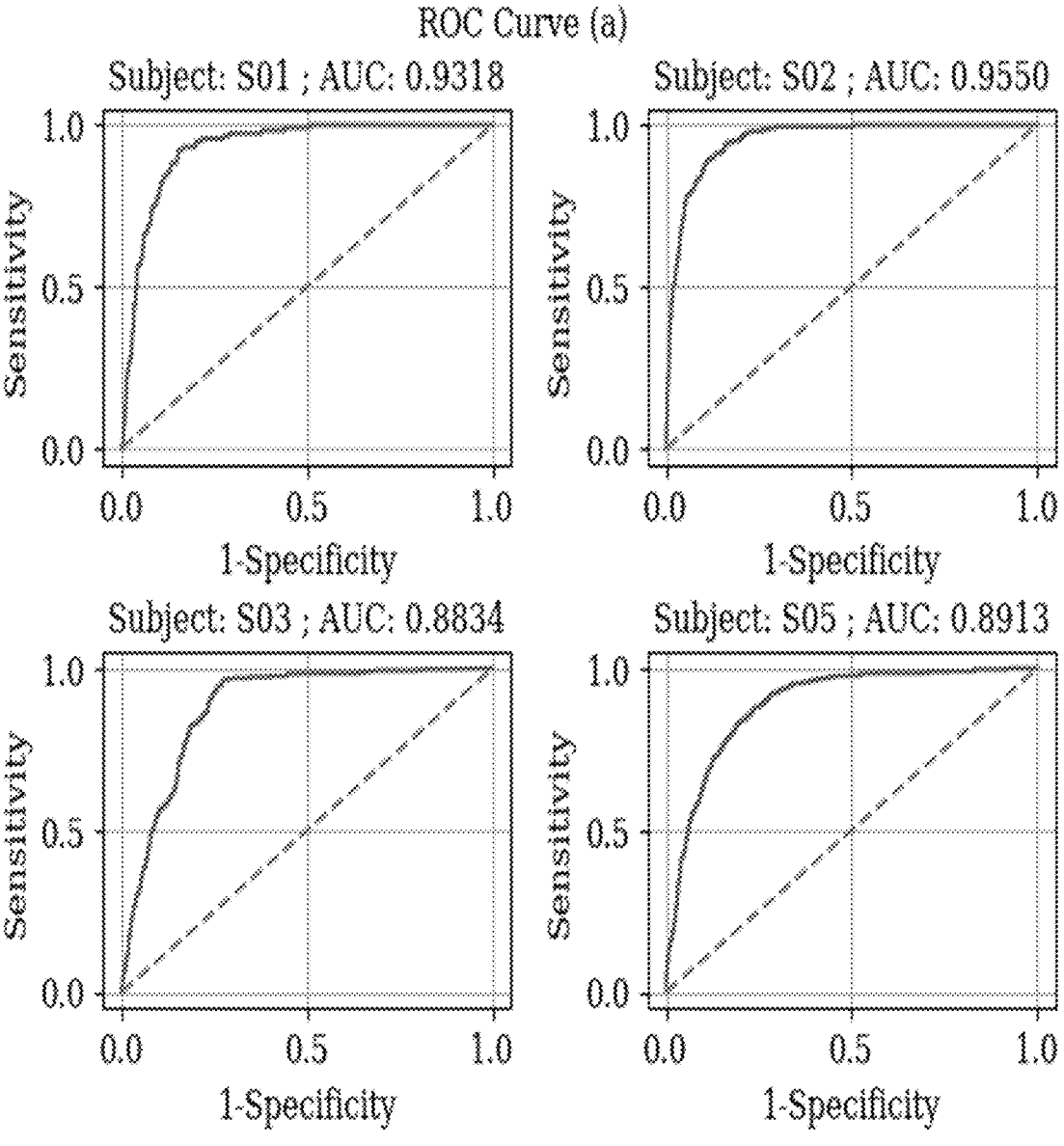
FIG. 5A and FIG. 5B illustrates example receiver operating characteristic (ROC) curves for classifier performance on various subject's motion data representing sensitivity versus specificity, in accordance with some embodiments of the present disclosure.
Figure 5B:
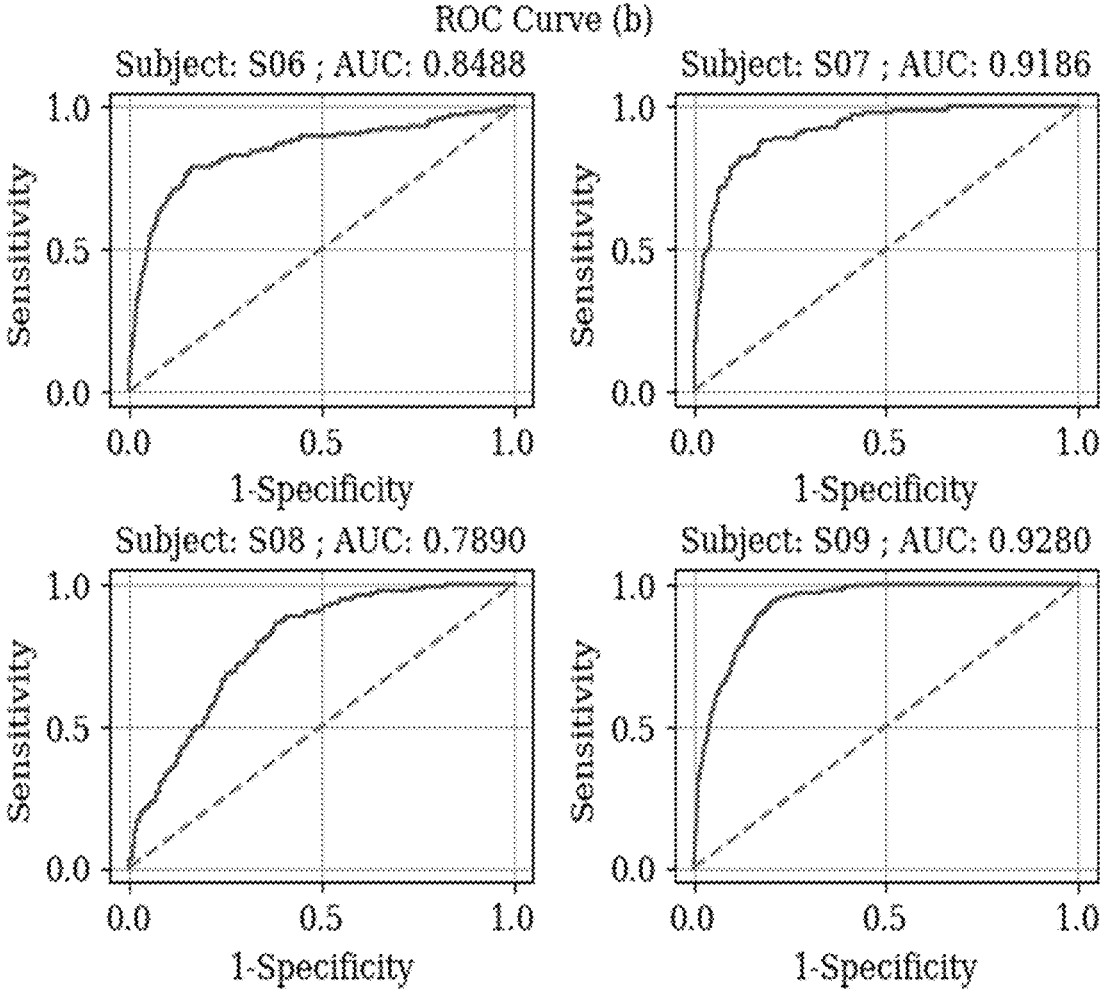

With the context of the present disclosure with Existing techniques 1-4, the Daphnet dataset with the patient-independent model setting and windows size (WS) as 4 sec. Referring now to Existing technique 1, leveraged the Freezing Index feature and reported the moderate accuracy on patient-independent model. Several patient-specific tunable parameters limit its generalization capability. Further, the existing technique 2 proposed a sophisticated machine learning-based approach and reported the best accuracy on specificity. However, this possess very poor result on sensitivity which is not desirable. As reported by existing technique 3-4, existing technique 2 chose sensitivity of 1.0 for subject 4 and subject 10 which improve its sensitivity results significantly. Referring now to (Existing techniques 3-4) extensive research work which incorporates the deep learning-based method (CNN) and offers remarkable performance in terms of sensitivity. This uses contextual windows (CW) which include features from adjacent time windows in classifier. The Existing technique 3, offers the best performance with three previous (PW) and three subsequent 4-second windows (SW) whereas the second result (Existing technique 4) is obtained with three previous (PW) windows only. Evidently, this contextual information increases the detection latency and hinders its applicability in a practical scenario. Moreover, the computational load and strenuous training phase are the two potential drawbacks of existing techniques 3-4. Incidentally, Existing technique 3-4, experimented and chosen an optimal threshold of probability scores of the classes to attain the highest sensitivity. This degrades the specificity considerably and increases the false alarm of FOG detection. For the sake of comparison, we have followed the same approach and reported the result (EWT [Algo-R1 and Algo-R2]) accordingly. The second result (EWT [Algo-R2]) is obtained with the default threshold of the pretrained classifier model. Comparing with the Existing technique 3-4, the first result (EWT [Algo-R1]) achieved the highest sensitivity. However, the specificity is slightly low. Although, the proposed method (Algo-R1 and Algo-R2) does not use any contextual windows and implicitly use only the present window for detection. This entails great advantage while deploying it in practice. The second proposed result (Algo-R2) also caters the balanced performance for both sensitivity and specificity. Apart from these works, another compelling approach employs unsupervised anomaly score detector (ASD) with adaptive thresholding to recognize the FOG events using the three IMU sensors. This approach achieved notable accuracy: (sensitivity:

0.87±0.16, specificity: 0.84±0.15) on the patient-independent model. However, the performance has been achieved with the longer window size of 8 seconds; implicating the higher detection latency. Moreover, comparatively, the proposed method (Algo-R1 and Algo-R2) caters lower standard deviation on both sensitivity and specificity, which manifests in better robustness of the algorithm. Also, this approach follows the different experimental protocol rather than exact LOSO approach. Notably, the proposed method (Algo-R1 and Algo-R2) has leveraged only the shank (above the ankle) sensor and exhibited the accuracy close to or better than others, who have used all three sensors. This further demonstrates the efficacy of the proposed method and makes it a more feasible approach. For further analysis, the performance of the individual subjects with the patient-independent model is plotted by utilizing the specificity vs sensitivity curve as shown in FIG. 5A and FIG. 5B. Subject 8 demonstrates the worst result whereas subject 2 exhibits the best. As reported in another existing technique subject 8 is greatly affected by PD (H&Y stage:4) and experiences great difficulty while walking. This conveniently explains the low performance of subject 8.

FIG. 5A and FIG. 5B illustrates example receiver operating characteristics (ROC) curve for classifier performance on various subject's motion data representing sensitivity versus specificity, in accordance with some embodiments of the present disclosure. Feature analysis: To analyze the impact of several features, four distinct experiments were performed. Each associated with one feature group. 1) Statistical feature group (SFG); 2) Physiological feature group (PFG); 3) Total feature group (TFG), a combination of both SFG and PFG, selected using RFE; 4) A subset of TFG feature group (STFG), which only excludes mean and median frequency. As shown in Table 2, integration of two new features mean and median frequency increases both Sensitivity and Specificity effectively.

TABLE 2

| Performance with different feature groups | | | | |
| --- | --- | --- | --- | --- |
| | SFG | PFG | STFG | TFG |
| SN | 0.73 | 0.81 | 0.80 | 0.83 |
| SP | 0.71 | 0.79 | 0.79 | 0.83 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of FOG detection from the motion data. The embodiment thus provides patient invariant model for freezing of gait detection based on empirical wavelet decomposition. Moreover, the embodiments herein further provide a FOG detection system integrated with two features to increase the fidelity of the EWT and the accuracy. Utilization of a single ankle sensor in the system provides a high degree of usability and reduces computational complexity. The proposed method is evaluated on Daphnet dataset achieving average sensitivity of about 0.95 and specificity of about 0.70 with a single ankle accelerometer sensor providing high potential of usability and accuracy. Further, to detect the FOG from motion data does not require any training data of the patient under test. The preprocessing layer discards outliers due to experimental malfunctioning. Further, the method proposes pertinent sub band features using the EWT and thereby employing random under sampling to handle class imbalance.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for freezing of gait (FOG) detection based on empirical wavelet decomposition, the method comprising:

receiving, via a one or more hardware processors, a motion data obtained from a sensor coupled to an ankle of a subject, wherein the sensor captures one or more activities performed by the subject, wherein the sensor comprises an accelerometer and the accelerometer sends the one or more activities performed by the subject in real time to a freezing of gait (FOG) detection system;

determining using a windowing, via the one or more hardware processors, a plurality of data windows from the motion data;

denoising using a peak detection technique, via the one or more hardware processors, the plurality of data windows by detecting total number of peaks associated with each data window is denoised using a peak detection technique, wherein each window is classified into one of (i) a real motion data window, if the number of candidate peaks are greater than one, or (ii) a noisy data window if the number of candidate peaks are lesser than or equal to one, wherein the candidate peak is identified if the peak height exceeds a predefined threshold estimated empirically in accordance with the real motion data window and the noisy data window;

discarding the noisy data window when the number of candidate peaks is less than or equal to one;

generating, using an empirical wavelet decomposition technique (EWT), via the one or more hardware processors, a plurality of denoised data windows based on (i) a spectrum associated with each real motion data window, and (ii) a plurality of empirical modes;

computing, via the one or more hardware processors, a resultant acceleration for each denoised data window based on a three axes motion data;

extracting, via the one or more hardware processors, a plurality of top ranked features, from the plurality of denoised data windows in time series, wherein the plurality of top ranked features comprises, (i) a plurality of statistical features, and (ii) a plurality of physiological features, wherein the plurality of top ranked features are selected based on a training data associated with a pretrained classifier model using a RFE technique;

detecting freezing of gait, via the one or more hardware processors, based on the pretrained classifier model and the plurality of features by classifying each denoised data window into at least one of (i) a positive class representing the FOG, or (ii) a negative class representing motion;

obtaining a first number of data windows with a ground truth label equal to 1 as the positive class and a second number of data windows with the ground truth label equal to 0 as the negative class;

detecting that the first number of data windows belonging to the positive class is greater than the second number of data windows belonging to the negative class being referred to as class imbalance;

applying a random under-sampling to randomly select and eliminate data windows of the positive class until the class is balanced, wherein the random under-sampling reduces computational overhead; and detecting the FOG from the motion data in absence of the training data of the subject under test and discarding the noisy data windows due to experimental malfunctioning, wherein utilization of the ankle sensor in the FOG detection system provides usability and reduces computational complexity.

2. The processor implemented method of claim 1, wherein the plurality of denoised data windows is generated using the empirical wavelet decomposition technique comprises:

segmenting, the spectrums obtained from the motion data into a plurality of contiguous segments, wherein the spectrums are obtained by applying Fourier transform;

constructing, a one or more empirical wavelets for each segment based on a segment boundary and a scaling function derived for each empirical wavelet based on a low pass filter and a band pass filter;

decomposing, the one or more empirical wavelets into at least one of each empirical mode from the plurality of empirical modes; and generating, the plurality of denoised data windows based on the empirical mode which have low frequency components, wherein selecting the first three empirical modes from the plurality of empirical modes which includes only low frequency components.

3. The processor implemented method of claim 2, wherein discarding the empirical mode which has high frequency components.

4. The processor implemented method of claim 1, wherein the plurality of physiological features includes a mean frequency, a median frequency, a freezing of gait power, a motion power and a freezing index.

5. The processor implemented method of claim 1, wherein the plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value.

6. The processor implemented method of claim 4, wherein the mean frequency is computed based on a frequency value and a spectral power of a power spectrum at each frequency bin.

7. The processor implemented method of claim 4, wherein the median frequency is computed based on the frequency value at which the power spectrum is divided into two regions with equal integral of the power.

8. A system for freezing of gait (FOG) detection based on empirical wavelet decomposition comprising:

a memory storing instructions;

one or more communication interfaces; and one or more hardware processors coupled to the memory via the one or more communication interfaces, wherein the one or more hardware processors are configured by the instructions to:

receive, a motion data obtained from a sensor coupled to an ankle of a subject, wherein the sensor captures one or more activities performed by the subject, wherein the sensor comprises an accelerometer and the accelerometer sends the one or more activities performed by the subject in real time to a freezing of gait (FOG) detection system;

determine using a windowing, a plurality of data windows from the motion data;

denoise using a peak detection technique, the plurality of data windows by detecting total number of peaks associated with each data window is denoised using a peak detection technique, wherein each window is classified into one of (i) a real motion data window, if the number of candidate peaks are greater than one, or (ii) a noisy data window if the number of candidate peaks are lesser than or equal to one, wherein the candidate peak is identified if the peak height exceeds a predefined threshold estimated empirically in accordance with the real motion data window and the noisy data window;

discard the noisy data window when the number of candidate peaks is less than or equal to one;

generate, using an empirical wavelet decomposition technique, a plurality of denoised data windows based on (i) a spectrum associated with each real motion data window, and (ii) a plurality of empirical modes;

compute, a resultant acceleration for each denoised data window based on a three axes motion data;

extract, a plurality of top ranked features, from the plurality of denoised data windows in time series, wherein the plurality of top ranked features comprises, (i) a plurality of statistical features, and (ii) a plurality of physiological features, wherein the plurality of top ranked features are selected based on a training data associated with a pretrained classifier model using a RFE technique; and detect freezing of gait, based on the pretrained classifier model and the plurality of features by classifying each denoised data window into at least one of (i) a positive class representing the FOG, or (ii) a negative class representing motion obtain a first number of data windows with a ground truth label equal to 1 as the positive class and a second number of data windows with the ground truth label equal to 0 as the negative class;

detect that the first number of data windows belonging to the positive class is greater than the second number of data windows belonging to the negative class being referred to as class imbalance;

apply a random under-sampling to randomly select and eliminate data windows of the positive class until the class is balanced, wherein the random under-sampling reduces computational overhead; and detect the FOG from the motion data in absence of the training data of the subject under test and discards the noisy data windows due to experimental malfunctioning, wherein utilization of the ankle sensor in the FOG detection system provides usability and reduces computational complexity.

9. The system as claimed in claim 8, wherein the plurality of denoised data windows is generated using the empirical wavelet decomposition technique comprises:

segmenting, the spectrums obtained from the motion data into a plurality of contiguous segments, wherein the spectrums are obtained by applying Fourier transform;

constructing, a one or more empirical wavelets for each segment based on a segment boundary and a scaling function derived for each empirical wavelet based on a low pass filter and a band pass filter;

decomposing, the one or more empirical wavelets into at least one of each empirical mode from the plurality of empirical modes; and generating, the plurality of denoised data windows based on the empirical modes which have low frequency components, wherein selecting the first three empirical modes from the plurality of empirical modes which includes only low frequency components, wherein the empirical mode which has high frequency components are discarded.

10. The system as claimed in claim 9, wherein the plurality of physiological features includes a mean frequency, a median frequency, a freezing of gait power, a motion power and a freezing index, wherein the mean frequency is computed based on a frequency value and a spectral power of a power spectrum at each frequency bin, wherein the median frequency is computed based on the frequency value at which the power spectrum is divided into two regions with equal integral of the power.

11. The system as claimed in claim 9, wherein the plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value.

12. One or more non-transitory machine readable information storage mediums comprising one or more instructions which when executed by one or more hardware processors cause:

receiving, a motion data obtained from a sensor coupled to an ankle of a subject, wherein the sensor captures one or more activities performed by the subject, wherein the sensor comprises an accelerometer and the accelerometer sends the one or more activities performed by the subject in real time to a freezing of gait (FOG) detection system;

determining using a windowing, a plurality of data windows from the motion data; denoising using a peak detection technique, the plurality of data windows by detecting total number of peaks associated with each data window is denoised using a peak detection technique, wherein each window is classified into one of (i) a real motion data window, if the number of candidate peaks are greater than one, or (ii) a noisy data window if the number of candidate peaks are lesser than or equal to one, wherein the candidate peak is identified if the peak height exceeds a predefined threshold estimated empirically in accordance with the real motion data window and the noisy data window;

discarding the noisy data window when the number of candidate peaks is less than or equal to one;

generating, using an empirical wavelet decomposition technique, a plurality of denoised data windows based on (i) a spectrum associated with each real motion data window, and (ii) a plurality of empirical modes;

computing, a resultant acceleration for each denoised data window based on a three axes motion data;

extracting, a plurality of top ranked features, from the plurality of denoised data windows in time series, wherein the plurality of top ranked features comprises, (i) a plurality of statistical features, and (ii) a plurality of physiological features, wherein the plurality of top ranked features are selected based on a training data associated with a pretrained classifier model using a RFE technique; and detecting freezing of gait, based on the pretrained classifier model and the plurality of features by classifying each denoised data window into at least one of (i) a positive class representing the FOG, or (ii) a negative class representing motion;

obtaining a first number of data windows with a ground truth label equal to 1 as the positive class and a second number of data windows with the ground truth label equal to 0 as the negative class;

detecting that the first number of data windows belonging to the positive class is greater than the second number of data windows belonging to the negative class being referred to as class imbalance;

applying a random under-sampling to randomly select and eliminate data windows of the positive class until the class is balanced, wherein the random under-sampling reduces computational overhead; and detecting the FOG from the motion data in absence of the training data of the subject under test and discarding the noisy data windows due to experimental malfunctioning, wherein utilization of the ankle sensor in the FOG detection system provides usability and reduces computational complexity.

13. The one or more non-transitory machine-readable information storage mediums of claim 12, wherein the plurality of denoised data windows is generated using the empirical wavelet decomposition technique comprises:

segmenting, the spectrums obtained from the motion data into a plurality of contiguous segments, wherein the spectrums are obtained by applying Fourier transform;

constructing, a one or more empirical wavelets for each segment based on a segment boundary and a scaling function derived for each empirical wavelet based on a low pass filter and a band pass filter;

decomposing, the one or more empirical wavelets into at least one of each empirical mode from the plurality of empirical modes; and generating, the plurality of denoised data windows based on the empirical mode which have low frequency components, wherein selecting the first three empirical modes from the plurality of empirical modes which includes only low frequency components.

14. The one or more non-transitory machine-readable information storage mediums of claim 13, wherein the plurality of physiological features includes a mean frequency, a median frequency, a freezing of gait power, a motion power and a freezing index.

15. The one or more non-transitory machine-readable information storage mediums of claim 13, wherein the plurality of physiological features includes a mean frequency, a median frequency, a freezing of gait power, a motion power and a freezing index, wherein the mean frequency is computed based on a frequency value and a spectral power of a power spectrum at each frequency bin, wherein the median frequency is computed based on the frequency value at which the power spectrum is divided into two regions with equal integral of the power.

16. The one or more non-transitory machine-readable information storage mediums of claim 13, wherein the plurality of statistical features includes a mean, a median, a standard deviation, a maximum value, a minimum value, and a range, wherein the maximum value is the highest value computed from the motion data and the resultant acceleration data, wherein, the minimum value is the lowest value computed from the motion data and the resultant acceleration data, wherein the range is the difference between the maximum value and the minimum value.

\* \* \* \* \*